(12) United States Patent
Banju et al.

(10) Patent No.: US 10,519,416 B2
(45) Date of Patent: Dec. 31, 2019

(54) FILTER FOR FILTRATION OF NUCLEATED CELLS AND FILTRATION METHOD USING THE SAME

(71) Applicant: Murata Manufacturing Co., Ltd., Nagaokakyo-shi, Kyoto-fu (JP)

(72) Inventors: Masaru Banju, Nagaokakyo (JP); Junko Watanabe, Nagaokakyo (JP); Takashi Kondo, Nagaokakyo (JP); Seiichi Matsumoto, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 16/110,167

(22) Filed: Aug. 23, 2018

(65) Prior Publication Data

US 2019/0017012 A1  Jan. 17, 2019

Related U.S. Application Data

(63) Continuation of application No. PCT/JP2017/010396, filed on Mar. 15, 2017.

(30) Foreign Application Priority Data

Mar. 18, 2016 (JP) .................. 2016-055479
Jun. 6, 2016 (JP) .................. 2016-112757

(51) Int. Cl.
| | |
|---|---|
| *C12M 1/00* | (2006.01) |
| *B01D 29/01* | (2006.01) |
| *B01D 39/20* | (2006.01) |
| *G01N 33/49* | (2006.01) |

(52) U.S. Cl.
CPC ............. *C12M 47/02* (2013.01); *B01D 29/01* (2013.01); *B01D 39/2027* (2013.01); *G01N 33/491* (2013.01); *B01D 2201/60* (2013.01)

(58) Field of Classification Search
None
See application file for complete search history.

(56) References Cited

U.S. PATENT DOCUMENTS

| | | | |
|---|---|---|---|
| 4,894,343 A | 1/1990 | Tanaka et al. | |
| 6,491,819 B2 | 12/2002 | Prince et al. | |
| 6,497,821 B1 | 12/2002 | Bellamy, Jr. et al. | |
| 8,273,253 B2 | 9/2012 | Curran | |
| 8,777,017 B2 | 7/2014 | Curran | |
| 2002/0033367 A1 | 3/2002 | Prince et al. | |
| 2004/0142463 A1 | 7/2004 | Walker et al. | |
| 2006/0252044 A1 | 11/2006 | Okamura et al. | |
| 2006/0254972 A1 | 11/2006 | Tai et al. | |
| 2007/0275156 A1 | 11/2007 | Tanaka et al. | |
| 2009/0269812 A1 | 10/2009 | Sawai et al. | |
| 2010/0143879 A1 | 6/2010 | Curran | |
| 2011/0177551 A1 | 7/2011 | Mimitsuka et al. | |
| 2013/0098827 A1 | 4/2013 | Curran | |
| 2014/0147883 A1 | 5/2014 | Prins et al. | |
| 2015/0111293 A1 | 4/2015 | Kanbara et al. | |
| 2015/0129769 A1 | 5/2015 | Kamba et al. | |
| 2015/0247802 A1 | 9/2015 | Ozasa | |
| 2016/0041075 A1 | 2/2016 | Kamba et al. | |
| 2016/0054223 A1 | 2/2016 | Kamba et al. | |
| 2016/0168601 A1 | 6/2016 | Mimitsuka et al. | |
| 2017/0137769 A1 | 5/2017 | Kikuhara et al. | |
| 2017/0247662 A1 | 8/2017 | Kanbara et al. | |
| 2017/0282180 A1 | 10/2017 | Yagi et al. | |

FOREIGN PATENT DOCUMENTS

| | | |
|---|---|---|
| DE | 202012003212 U1 | 7/2012 |
| EP | 3031903 A1 | 6/2016 |
| JP | H02043911 A | 2/1990 |
| JP | 2000501338 A | 2/2000 |
| JP | 2005152527 A | 6/2005 |
| JP | 2007252367 A | 10/2007 |
| JP | 2008023469 A | 2/2008 |
| JP | 2008048721 A | 3/2008 |
| JP | 2008237213 A | 10/2008 |
| JP | 2009284860 A | 12/2009 |
| JP | 2010520446 A | 6/2010 |
| JP | 2013215109 A | 10/2013 |
| JP | 2013541958 A | 11/2013 |
| JP | 2013255487 A | 12/2013 |
| JP | 2014523534 A | 9/2014 |
| JP | 2015192642 A | 11/2015 |
| JP | 2016052300 A | 4/2016 |
| JP | 2016086736 A | 5/2016 |
| JP | 2016103982 A | 6/2016 |
| WO | 2007097260 A1 | 8/2007 |
| WO | 2010038613 A1 | 4/2010 |
| WO | 2013172265 A1 | 11/2013 |
| WO | 2014017430 A1 | 1/2014 |
| WO | 2014192389 A1 | 3/2014 |
| WO | 2014192917 A1 | 12/2014 |
| WO | 2016031971 A1 | 3/2016 |
| WO | 2016158793 A1 | 10/2016 |

OTHER PUBLICATIONS

Medical equipment News: "Murata PM 25 can also be detected, Murata Manufacturing unveils standard products of metal mesh devices"; <http://monoist.atmarkit.co./jp/mn/articles/1409/03/news128.html> (Retrieved Oct. 27, 2016—5 pages).

(Continued)

*Primary Examiner* — Blaine Lankford
(74) *Attorney, Agent, or Firm* — Arent Fox LLP

(57) ABSTRACT

A filtration method for filtration of nucleated cells that includes providing a filter containing at least one of a metal and a metal oxide as a major component thereof and having a plurality of through-holes therein, and passing a liquid containing the nucleated cells through the filter. The diameter of an inscribed circle of each of the plurality of through-holes is smaller than the size of the nuclei of the nucleated cells, and the inscribed circle of each of the plurality of through-holes touches all sides defining an opening of the through-hole.

8 Claims, 3 Drawing Sheets

(56) References Cited

OTHER PUBLICATIONS

Medical equipment News: "Murata PM 25 can also be detected, Murata Manufacturing unveils standard products of metal mesh devices"; <http://monoist/atmarkit.co.jp/mn/articles/1409/03/news128.html> (Retrieved Apr. 30, 2018—9 pages).

Chaitanya Katak et al.; "Lab-on-a-chip technology: impacting non-invasive prenatal diagnostics (NIPD) through miniaturisation"; The Royal Society of Chemistry 2014, Lap Chip, 2014, pp. 841-854.

FILTER FOR FILTRATION OF NUCLEATED CELLS AND FILTRATION METHOD USING THE SAME

CROSS REFERENCE TO RELATED APPLICATIONS

The present application is a continuation of International application No. PCT/JP2017/010396, filed Mar. 15, 2017, which claims priority to Japanese Patent Application No. 2016-055479, filed Mar. 18, 2016, and Japanese Patent Application No. 2016-112757, filed Jul. 6, 2016, the entire contents of each of which are incorporated herein by reference.

FIELD OF THE INVENTION

The present invention relates to filters for filtration of nucleated cells and to filtration methods using such filters.

BACKGROUND OF THE INVENTION

Patent Document 1 discloses a method for concentrating mononuclear cells and platelets from a liquid containing red blood cells, nucleated cells, and platelets through a cell capture filter material. The cell capture filter material in Patent Document 1 captures nucleated cells and platelets while allowing unnecessary cells, such as red blood cells, to pass therethrough.

Patent Document 1: Japanese Unexamined Patent Application Publication No. 2009-284860

SUMMARY OF THE INVENTION

Unfortunately, the cell capture filter material in Patent Document 1 still leaves room for improvement, particularly with regard to improved recovery of nucleated cells.

An object of the present invention is to provide a filter for filtration of nucleated cells that allows for improved recovery of nucleated cells and a filtration method using such a filter.

A filter according to one aspect of the present invention is a filter for filtration of nucleated cells, wherein the filter contains at least one of a metal and a metal oxide as a major component thereof, wherein the filter has a plurality of through-holes formed therein, and wherein the diameter of an inscribed circle of each of the plurality of through-holes is smaller than the size of nuclei of the nucleated cells, the inscribed circle of each of the plurality of through-holes touching all sides defining an opening of the through-hole.

A filtration method, according to one aspect of the present invention is a method for filtration of nucleated cells that includes providing a filter containing at least one of a metal and a metal oxide as a major component and having a plurality of through-holes formed therein, wherein the diameter of an inscribed circle of each of the plurality of through-holes is smaller than the size of nuclei of the nucleated cells, the inscribed circle of each of the plurality of through-holes touching all sides defining an opening of the through-hole; and passing a liquid containing the nucleated cells through the filter.

According to the present invention, a filter for filtration of nucleated cells that allows for improved recovery of nucleated cells and a filtration method using such a filter can be provided.

DETAILED DESCRIPTION OF THE PREFERRED EMBODIMENTS

Figure 1:
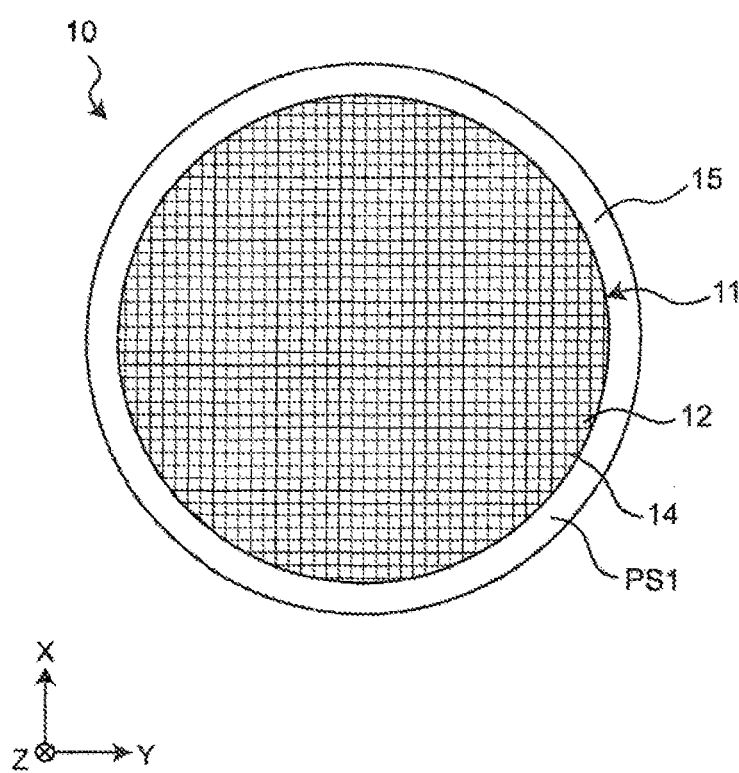
FIG. 1 is a schematic configuration view of a filter according to a first embodiment or the present invention.

According to Patent Document 1, a cell capture filter material formed of nonwoven fabric is used to capture nucleated cells and platelets while allowing unnecessary calls, such as red blood cells, to pass therethrough, thereby separating mononuclear cells from blood. Unfortunately, the cell capture filter in Patent Document 1 recovers only about 74% of the mononuclear cells; thus, this filter still leaves room for improvement, particularly with regard to improved recovery of the cells to be captured.

After conducting extensive research, the inventors have discovered that the filtration of a liquid containing nucleated cells through a filter containing at least one of a metal and a metal oxide as a major component allows for improved recovery of the nucleated cells to be captured. This discovery has led to the present invention.

A filter according to one aspect of the present invention is a filter for filtration of nucleated cells, wherein the filter contains at least one of a metal and a metal oxide as a major component, wherein the filter has a plurality of through-holes formed therein, and wherein the diameter of an inscribed circle of each of the plurality of through-holes is smaller than the size of nuclei of the nucleated cells, the inscribed circle of each of the plurality of through-holes touching all sides defining an opening of the through-hole.

This configuration improves the recovery of the nucleated cells.

In this filter, the ratio of the diameter of the inscribed circle of each through-hole to the size of the nuclei of the nucleated cells may be 0.64 or less.

This configuration further improves the recovery of the nucleated cells.

In this filter, the ratio of the diameter of the inscribed circle of each through-hole to the size of the nuclei of the nucleated cells may be 0.06 or more.

This configuration further improves the recovery of the nucleated cells.

In this filter, the ratio of the diameter of the inscribed circle of each through-hole to the size of the nuclei of the nucleated cells may be 0.07 or more.

This configuration shortens the filtration time and further improves the recovery of the nucleated cells.

This filter may have a smooth main surface for contact with a liquid containing the nucleated cells.

This configuration facilitates recovery of nucleated cells captured on the main surface of the filter section.

In this filter, the immersion potential of the at least one of the metal and the metal oxide in phosphate-buffered saline may be higher than 0.03 V with respect to a silver chloride reference electrode immersed in a saturated potassium chloride solution.

This configuration prevents the metal or metal oxide present as a filter component from dissolving in a liquid containing nucleated cells.

In this filter, the at least one of the metal and the metal oxide may contain at least one selected from the group consisting of gold, silver, copper, platinum, nickel, palladium, and alloys and oxides thereof.

This configuration further improves the recovery of the nucleated cells.

A filtration method according to one aspect of the present invention is a method for filtration of nucleated cells that includes providing a filter containing at least one of a metal and a metal oxide as a major component and having at plurality of through-holes formed therein, wherein the diameter of an inscribed circle of each of the plurality of through-holes is smaller than the size of nuclei of the nucleated cells, the inscribed circle of each of the plurality of through-holes touching all sides defining an opening of the through-hole; and passing a liquid containing the nucleated cells through the filter.

This configuration improves the recovery of the nucleated cells.

In this filtration method, the ratio of the diameter of the inscribed circle of each through-hole to the size of the nuclei of the nucleated cells may be 0.64 or less.

This configuration further improves the recovery of the nucleated cells.

In this filtration method, the ratio of the diameter of the inscribed circle of each through-hole to the size of the nuclei of the nucleated cells may be 0.06 or more.

This configuration further improves the recovery of the nucleated cells.

In this filtration method, the ratio of the diameter of the inscribed circle of each through-hole to the size of the nuclei of the nucleated cells may be 0.07 or more.

This configuration shortens the filtration time and further improves the recovery of the nucleated cells.

In this filtration method, the filter may have a smooth main surface for contact with the liquid containing the nucleated cells.

This configuration facilitates recovery of nucleated cells captured on the main surface of the filter.

In this filtration method, the immersion potential of the at least one of the metal and the metal oxide in phosphate-buffered saline may be higher than 0.03 V with respect to a silver chloride reference electrode immersed in a saturated potassium chloride solution.

This configuration prevents the metal or metal oxide present as a filter component from dissolving in the liquid containing the nucleated cells.

In this filtration method, the at least one of the metal and the metal oxide may contain at least one selected from the group consisting of gold, silver, copper, platinum, nickel, palladium, and alloys and oxides thereof.

This configuration further improves the recovery of the nucleated cells.

In this filtration method, the step of passing the liquid containing the nucleated cells through the filter may include a step of separating living cells and dead cells.

This configuration allows living cells and dead cells to be separated.

In this filtration method, the coefficient of variation of the size of the plurality of through-holes in the filler may be 0.17 or less.

This configuration further improves the recovery of the nucleated cells.

In this filtration method, the through-holes in the filter may have a regular polygonal shape.

This configuration further improves the recovery of the nucleated cells.

In this filtration method, the through-holes in the filter may have a square shape.

This configuration further improves the recovery of the nucleated cells.

A kit according to one aspect of the present invention for performing the above filtration method includes a filter for filtration of nucleated cells, wherein the filter contains at least one of a metal and a metal oxide as a major component, wherein the filter has a plurality of through-holes formed therein, and wherein the diameter of an inscribed circle of each of the plurality of through-holes is smaller than the size of nuclei of the nucleated cells, the inscribed circle of each of the plurality of through-holes touching all sides defining an opening of the through-hole.

This configuration improves the recovery of the nucleated cells.

A first embodiment of the present invention will now be described with reference to the accompanying drawings. In the drawings, the elements are shown in exaggerated form for ease of description.

First Embodiment

Filter Configuration

Figure 2:
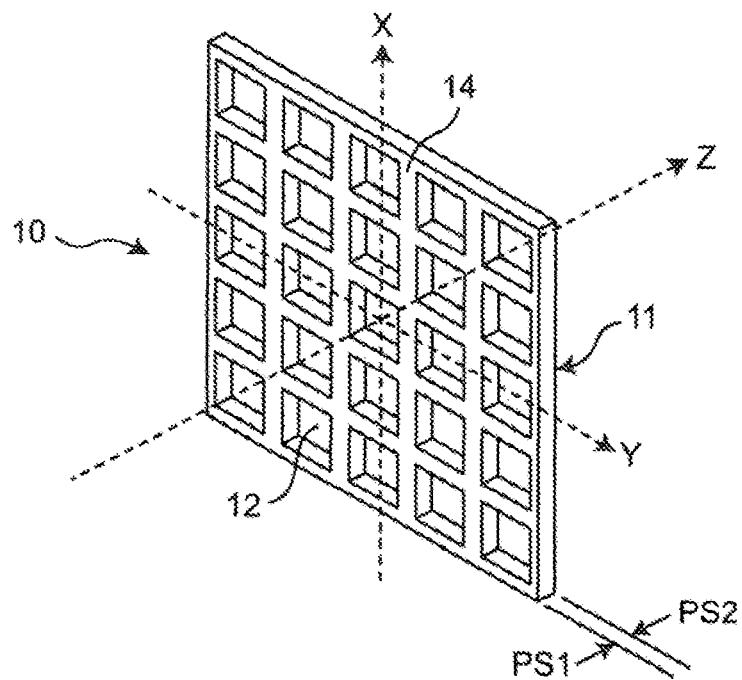
FIG. 2 is an enlarged perspective view of a portion of the filter according to the first embodiment of the present invention.

FIG. 1 is a schematic configuration view of a filter 10 according to the first embodiment of the present invention. FIG. 2 is an enlarged perspective view of a portion of the filter 10 according to the first embodiment of the present invention. The X-, Y-, and Z-directions in FIGS. 1 and 2 indicate the vertical, horizontal, and thickness directions, respectively, of the filter 10. As shown in FIG. 1, the filter 10 includes a filter section 11 and a frame section 15 disposed around the filter section 11. As shown in FIG. 2, the filter 10 has opposing first and second main surfaces PS1 and PS2. The filter section 11 includes a filter body 14 having a plurality of through-holes 12 formed, through the first and second, main surfaces PS1 and PS2. The diameter of the inscribed circle of each through-hole 12 is set to be smaller than the size of the nuclei of the nucleated cells.

The filter 10 allows a liquid containing nucleated cells (cell suspension) to pass through the filter section 11 to filter the nucleated cells.

As used herein, the term "nucleated cell" refers to a cell in which a nucleolus is separated from cytoplasm by a nuclear membrane.

Material

The filter body 14, which forms the body of the filter 10, is formed of a material containing a metal and/or a metal oxide as a major component. For example, the filter body 14 may be formed of gold, silver, copper, platinum, nickel, palladium, or an alloy or oxide thereof.

The outermost layer of the filter 10 may be formed of a metal and/or metal oxide that does not readily dissolve in cell suspensions. For example, if the outermost layer of the filter 10 is a coating of a metal whose immersion potential in phosphate-buffered saline is higher than 0.03 V with respect to a silver chloride reference electrode immersed in a saturated potassium chloride solution, the coating inhibits the dissolution of the material forming the filter 10 in cell suspensions. This reduces stress on the cells. Alternatively, the outermost layer of the filter 10 may be formed of a hydrophilic material. For example, this shortens the time for treatment of an aqueous cell suspension and thus reduces stress on the cells.

Outer Shape

The outer shape of the filter 10 is, for example, circular, rectangular, or oval. In the first embodiment, the outer shape of the filter 10 is substantially circular. If the outer shape of the filter 10 is substantially circular, fluid can uniformly flow through one main surface of the filter 10 (e.g., the first main surface PS1 of the filter section 11). As used herein, the term "substantially circular" refers to a shape having a ratio of the length of the major axis to the length of the minor axis of from 1.0 to 1.2.

Filter Section

The filter section 11 is a plate-like structure having the plurality of through-holes 12 formed therein. The shape of the filter section 11 is, for example, circular, rectangular, or oval. In the first embodiment, the shape of the filter section 11 is substantially circular. If the shape of the filter section 11 is substantially circular, fluid can uniformly flow through the first main surface PS1 of the filter section 11.

Figure 3:
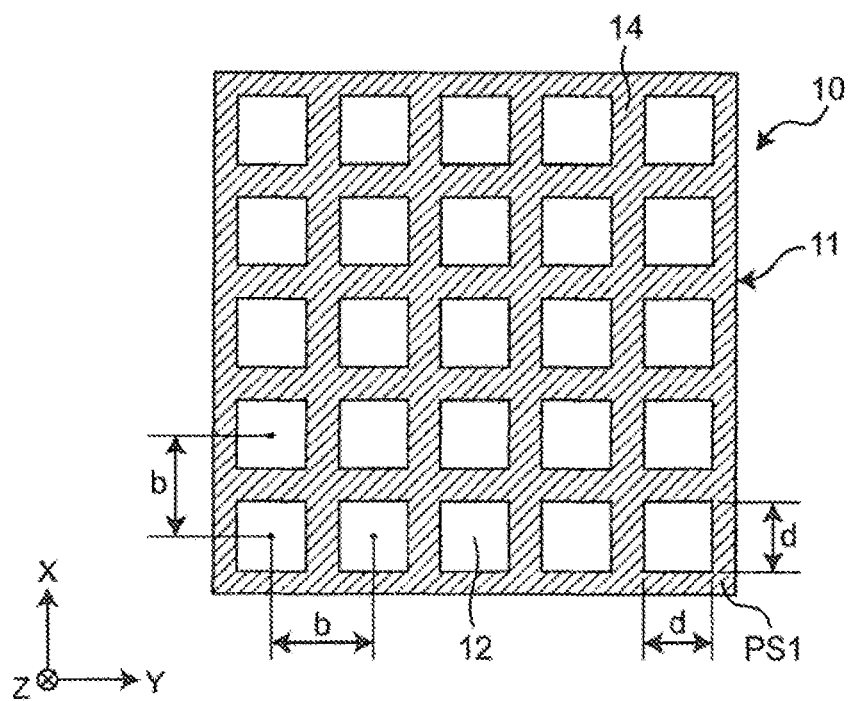
FIG. 3 is a schematic view of a portion of the filter in FIG. 2 as viewed in the thickness direction.

FIG. 3 is a schematic view of a portion of the filter section 11 as viewed in the thickness direction (Z-direction). As shown in FIG. 3, the plurality of through-holes 12 are arranged in a periodic array in the first and second main surfaces PS1 and PS2 of the filter section 11. Specifically, the plurality of through-holes 12 are arranged in a matrix at regular intervals in the filter section 11.

In the first embodiment, the through-holes 12 have a square shape as viewed from the first main surface PS1 side of the filter section 11, i.e., in the Z-direction. The through-holes 12, however, need not have a square shape as viewed in the Z-direction, but may have other shapes such as triangles, rhombuses, and regular polygons.

In the first embodiment, the through-holes 12 have a rectangular shape (cross-sectional shape) as projected onto a plane perpendicular to the first main surface PS1 of the filter section 11. Specifically, the through-holes 12 have a rectangular cross-sectional shape that is longer on one side in the radial direction of the filter 10 than on one side in the thickness direction of the filter 10. The through-holes 12, however, need not have a rectangular cross-sectional shape, but may have other cross-sectional shapes such as parallelograms and tapered shapes, such as trapezoids, and may be either symmetrical or asymmetrical.

In the first embodiment, the plurality of through-holes 12 are arranged at the same pitch in two array directions parallel to the sides of the squares as viewed from the first main surface PS1 side of the filter section 11 (Z-direction), i.e., in the X- and Y-directions in FIG. 3. If the plurality of through-holes 12 are arranged in a square grid array in this way, the open area percentage can be improved, thus reducing the resistance of the filter 10 to the passage of fluid. This configuration shortens the treatment time and thus reduces stress on the cells. This configuration also improves the symmetry of the array of through-holes 12 and thus facilitates observation of the filter.

The plurality of through-holes 12, however, need not be arranged in a square grid array, but may be arranged in, for example, a quasiperiodic or periodic array. Examples of periodic arrays include quadrangular arrays such as rectangular arrays, which have different pitches in two array directions, and triangular or regular triangular grid arrays. The through-holes 12 may be arranged in any array, provided that a plurality of through-holes 12 are provided in the filter section 11.

The pitch of the through-holes 12 is appropriately set depending on the type (size, morphology, properties, and elasticity) and quantity of the cells to be separated. Here, as shown in FIG. 3, the pitch of the through-holes 12 refers to the distance b between the center of any through-hole 12 and the center of an adjacent through-hole 12 as the through-holes 12 are viewed from the first main surface PS1 side of the filter section 11. For structures having a periodic array, the pitch b of the through-holes 13 is, for example, more than 1 to 10 times, preferably 3 or more times, the length d on one side of each through-hole 12. Alternatively, the filter section 11 has an open area percentage of, for example, 10% or more, preferably 25% or more. This configuration reduces the resistance of the filter section 11 to the passage of fluid, thus shortening the treatment time and reducing stress on the cells. The open area percentage is calculated as (area occupied by through-holes 12)/(projected area of first main surface PS1 on assumption that no through-holes 12 are provided).

The diameter of the inscribed circle of each through-hole 12 is set to be smaller than the size of the nuclei of the nucleated cells. As used herein, the term "inscribed circle of each through-hole 12" refers to a circle having the largest diameter of all circles that can be drawn within the through-hole 12 as viewed from the first main surface PS1 side of the filter section 11, i.e., a circle having the largest diameter of all circles touching the inner wall of the filter section 11 forming the through-hole 12. In other words, the term "inscribed circle of each through-hole 12" refers to a circle touching all sides defining the opening of the through-hole 12 as viewed from the first main surface PS1 side of the filter section 11. As used herein, the term "size of the nuclei of the nucleated cells" refers to the average length of the nuclei of a plurality of nucleated cells measured in liquid by observation under a microscope. The length of the nucleus of each nucleated cell is measured as the length of a line that is the longest of all lines connecting any two points on the perimeter of the nucleus of the nucleated cell.

The dimensions of the through-holes 12 are preferably set such that the ratio of the diameter of the inscribed circle of each through-hole to the size of the nuclei of the nucleated cells is 0.64 or less. The ratio of the diameter of the inscribed circle of each through-hole 12 to the size of the nuclei of the nucleated cells is also preferably 0.06 or more. More preferably, the ratio of the diameter of the inscribed circle of each through-hole 12 to the size of the nuclei of the nucleated cells is 0.07 or more.

The dimensions of the plurality of through-holes 12 are set to be substantially identical. If a plurality of through-holes 12 having the same shape are arranged in a periodic array, a lower standard deviation of the dimensions of the plurality of through-holes 12 is preferred. Specifically, the coefficient of variation calculated from the average and the standard deviation of the measured lengths d on one side of 100 through-holes 12 is preferably 40% or less.

The thickness of the filter section 11 is preferably more than 0.1 to 100 times the size (length d on one side) of each through-hole 12. More preferably, the thickness of the filter section 11 is more than 0.5 to 10 times the size (length d on one side) of each through-hole 12. This configuration reduces the resistance of the filter 10 to the passage of fluid and thus shortens the treatment time. As a result, stress on the cells can be reduced.

The arithmetic mean roughness of the surface (first main surface PS1) of the filter section 11 is preferably smaller than the size of the nuclei of the nucleated cells. This configuration reduces the adhesion of the cells to the surface (first main surface PS1) of the filter section 11 and thus increases the recovery of the cells. The arithmetic mean roughness of the filter section 11 is calculated as the average of measurements taken at five points on the surface of the filter section 11 using a DEKTAK 150 (registered trademark) stylus profilometer available from ULVAC, Inc.

The first main surface PS1 of the filter section 11, which is a surface for contact with a liquid containing nucleated cells, may be formed as a smooth surface. Specifically, the first main surface PS1 of the filter section 11 may be formed as a uniform, flat surface without irregularities. In other words, the openings of the plurality of through-holes 12 in the first main surface PS1 of the filter section 11 are formed in the same plane. The filter body 14, which is the portion of the filter section 11 where no through-holes 12 are formed, is continuous and formed as one piece. This configuration reduces the adhesion of the cells to the surface (first main surface PS1) of the filter section 11 and thus facilitates recovery of captured nucleated cells.

The openings of the through-holes 12 on the first main surface PS1 side and the second main surface PS2 side of the filter section 11 communicate with each other via continuous wall surfaces. Specifically, the through-holes 12 are provided such that the openings thereof on the first main surface PS1 side can be projected onto the openings thereof on the second main surface PS2 side. That is, the through-holes 12 are provided such that the openings thereof on the first main surface PS1 side are superposed on the openings thereof on the second main surface PS2 side as the filter section 11 is viewed from the first main surface PS1 side. In the first embodiment, the through-holes 12 are provided such that the inner walls thereof are perpendicular to the first and second main surfaces PS1 and PS2.

Frame Section

The frame section 15 is disposed around the filter section 11 and has fewer through-holes 12 per unit area than the filter section 11. The number of through-holes 12 in the frame section 15 is 1% or less of the number of through-holes 12 in the filter section 11. The frame section 15 may be thicker than the filter section 11. This configuration improves the mechanical strength of the filter 10.

If the filter 10 is connected to an apparatus during use, the frame section 15 may function as a connection to connect the filter 10 to the apparatus. Filter information (e.g., the dimensions of the through-holes 12) may also be displayed on the frame section 15.

The frame section 15 is formed in an annular shape as viewed from the first main surface PS1 side of the filter section 11. As the filter 10 is viewed from the first main surface PS1 side, the center of the frame section 15 coincides with the center of the filter section 11. That is, the frame section 15 is formed concentrically with the filter.

From the viewpoint of ease of handling and connection to a system, the filter 10 may be attached to a jig during use. The jig may be formed of, for example, a material that can be sterilized with gamma radiation. For example, the jig may be formed of a material containing polyethylene, polyethylene terephthalate, polyurethane, polystyrene, silicone rubber, ABS resin, polyamide, polyamide-imide, polysulfone, natural rubber, latex, urethane rubber, silicone rubber, ethylene-vinyl acetate, polyester, epoxy, phenolic, silica, alumina, gold, platinum, nickel, stainless steel, titanium, or the like. The use of such a material for the jig reduces stress on the cells.

Filtration Method

A filtration method using the filter 10 will now be described.

The filter 10 is first provided. In this step, a filter 10 having through-holes 12 whose size is selected depending on the size of the nuclei of the nucleated cells is provided. Specifically, a filter 10 having through-holes 12 smaller than the size of the nuclei of the nucleated cells to be filtered is provided.

For example, in the step of providing the filter 10, a filter 10 having through-holes 12 whose size is smaller than the size of the nuclei of the nucleated cells may be selected after the size of the nuclei of a plurality of nucleated cells is determined, for example, using a micrometer or hemocytometer. Alternatively, a filter 10 having through-holes 12 whose size is smaller than the size of the nuclei of the nucleated cells may be selected after photographs of a plurality of nucleated cells are captured and the size of the nuclei of the plurality of nucleated cells is determined. The filter 10 may also be selected in any other manner.

The filter 10 is attached to an apparatus. Specifically, the filter 10 is attached to the apparatus by holding the frame section 15 of the filter 10.

A cell suspension is then passed through the filter 10. As used herein, the term "cell suspension" refers to a fluid containing nucleated cells. In many cases, the fluid containing the nucleated cells is a liquid. Examples of liquids include culture solutions, phosphate-buffered saline, and water containing substances such as amino acids, proteins, and serum. In addition to the cells and the fluid, the cell suspension may contain nonbiological substances such as resin particles, pieces of tissues such as bone and flesh, dead cells, and the like.

In this way, the liquid containing the nucleated cells is passed through the filter section 11 to separate the nucleated cells from the liquid. In the first embodiment, the diameter of the inscribed circle of each through-hole 12 in the filter section 11 is set to be smaller than the size of the nuclei of the nucleated cells. Thus, the nucleated cells are captured on the first main surface PS1 of the filter section 11 without passing through the through-holes 12.

An example method for passing the cell suspension through the filter 10 involves passing the cell suspension through the filter section 11 from above the first main surface PS1 substantially vertically under gravity. Another method involves passing the cell suspension through the filter 10 by bringing the cell suspension into contact with the first main surface PS1 of the filter section 11 and applying pressure to the cell suspension (pressing). Still another method involves passing the cell suspension through the filter 10 by bringing the cell suspension into contact with the first main surface PS1 of the filter section 11 and applying suction from the second main surface PS2 (suction). In the step of passing the liquid containing the nucleated cells through the filter section 11, it is preferred to minimize the stress applied to the cells. For example, if pressure is applied, the pressure is preferably low enough to prevent deformation of the nucleated cells. More preferably, the liquid is passed through the filter section 11 under its own weight without applying pressure. It is also preferred to increase the open area percentage of the filter section 11 to shorten the treatment time and thereby reduce the period of time during which stress is being applied to the nucleated cells.

The cell suspension may also be passed through the filter 10 while the nucleated cells are floating in the liquid. Since the nucleated cells floating in the liquid become nearly spherical, the recovery of the nucleated cells to be captured, can be improved. That is, the dimensional accuracy of the nucleated cells to be captured can be improved.

The cell suspension may also be passed through the filter 10 multiple times so that the dimensional accuracy of the nucleated cells to be captured can be improved.

In the filtration method using the filter 10, filtration may be performed, for example, using a filtration container. For example, the filtration container may be a cylindrical container having an outer shape of 14 mm, an inner diameter of 6 mm, and a height of 55 mm, with the filter 10 attached to the bottom thereof. The filtration container, however, need not be this type of container, but may have various shapes and dimensions.

Method for Manufacturing Filter

A typical method for manufacturing the filter 10 will now be described. The filter 10 is manufactured by the following process.

Formation of Current Supply Film

A Cu current supply film is formed on the top surface of a silicon substrate using a sputtering apparatus. This current supply film serves as a current source during the formation of the filter body 14 of the filter 10, as described later. In this step, an intermediate layer such as a Ti layer may also be formed in order to ensure sufficient adhesion between the silicon substrate and the current supply film.

The Cu current supply film is formed under the following conditions:
Sputtering gas: argon gas
Degree of vacuum of sputtering apparatus: $5.0 \times 10^{-4}$ Pa
Applied power: DC 500 W
Sputtering time:
27 minutes for formation of Cu film
3 minutes and 5 seconds for formation of Ti film

Formation of Resist Image

A resist image is formed on the current supply film formed on the top surface of the silicon substrate.

A resist film having a predetermined thickness is formed on the current supply film formed on the top surface of the silicon substrate, for example, using a spin coater. The resist is then exposed through a photomask having a predetermined pattern formed therein and is developed to form a resist image.

The resist film is applied under the following conditions:
Resist: novolac resin with organic solvent
Rotational speed of spin coater: 1,130 rpm
Resist film thickness: 2 μm After the resist is applied to the top surface of the silicon substrate using a spin coater, the solvent is evaporated at 130° C. in a nitrogen atmosphere, followed by cooling to form a resist film.

The resist is exposed to light containing a component with a wavelength of 365 nm and having an energy density of 2,500 $J/m^2$ for 0.25 second.

The resist is developed by bringing the exposed portion into contact with an alkaline solution.

Formation of Filter Body

The filter body 14 is formed in the opening in the resist image. A filter body 14 formed of a nickel coating is formed by electroplating using the current supply film formed in advance as a current source.

The filter body 14 is formed under the following conditions:
Pretreatment: immersed in dilute sulfuric acid for 60 seconds to activate the surface of the current supply film
Plating solution: nickel sulfamate plating solution, liquid temperature=55° C., pH=4.0
Plating rate: 0.5 μm/min
Plating: electroplating with shaking

Dissolution and Stripping of Resist

The filter body 14 is sonicated in acetone solution for 15 minutes to dissolve the resist film and thereby strip the resist.

Formation of Support Substrate

A support substrate may optionally be provided on the filter 10 for filtration using the filter 10. This prevents the filter 10 from being damaged during filtration. The support substrate is fabricated by the following process. The support substrate corresponds to a member indicated by reference sign "13" in FIG. 4, described later.

After a photosensitive resist is applied again to the top surface of the silicon substrate having the body of the filter 10 formed thereon to form a resist film, the resist is exposed through a photomask and is developed to form a resist image. In this step, exposure and development are performed such that the resist image extends across a plurality of portions of the body of the filter 10. The areas where the resist image extends across the body of the filter 10 correspond to the openings in the finished filter 10. That is, the number of portions of the body of the filter 10 across which the resist image extends is appropriately determined depending on the required open area percentage of the filter 10.

The filter body 14 is formed in the opening in the resist image. A support substrate formed of a nickel coating is formed by electroplating using the current supply film formed in advance as a current source. The width of the support substrate is appropriately determined depending on the required strength of the filter 10.

The support substrate is sonicated in acetone solution for 15 minutes to dissolve the resist film and thereby strip the resist.

Removal of Current Supply Film

The current supply film is removed, and the filter body 14 and the support, substrate are separated from the silicon substrate. The filter 10 for filtration of nucleated cells is finished.

The current supply film is removed by immersion in an aqueous solution prepared from 60% aqueous hydrogen peroxide, acetic acid, and pure water in a mixing ratio of 1:1:20 in an environment at 25° C. for 48 hours.

The filter 10 according to the first embodiment provides the following advantageous effects.

The filter 10 contains at least one of a metal and a metal oxide as a major component. The filter 10 also includes the filter section 11 having the plurality of through-holes 12 formed therein. This configuration captures the nucleated cells to be captured with little deformation of the through-holes 12 in the filter section 11, thus improving the recovery of the nucleated cells.

The diameter of the inscribed circle of each through-hole 12 is set to be smaller than the size of the nuclei of the nucleated cells. This configuration further improves the recovery of the nucleated cells.

The first main surface PS1 of the filter section 11 is formed as a smooth surface. This configuration allows nucleated cells captured on the first main surface PS1 to be easily separated from the filter section 11, thus facilitating the recovery thereof.

There are nucleated cells having nuclei of various shapes other than perfect circles, such as ovals. The through-holes 12 are formed in the filter 10 such that the diameter of the inscribed circle of each through-hole 12 is smaller than the size of the nuclei of the nucleated cells. The inscribed circle of each through-hole 12 touches all sides defining the opening of the through-hole 12. This configuration allows nuclei of various shapes other than perfect circles to be reliably captured, thus improving the recovery thereof.

In the filtration method using the filter 10, a liquid containing nucleated cells is passed through the filter 10. This allows the nucleated cells to be reliably captured, thus improving the recovery thereof.

Nucleated cells have nuclei of various sixes depending on the type, culture conditions, number of passages, and other factors. For example, the nucleus size varies depending on culture conditions such as culture temperature, time, and environment for the same cell. Since nucleated cells have nuclei of various sizes, they may pass through the through-holes 12 if the filter 10 is provided without consideration of the nucleus size. In the filtration method using the filter 10, a filter 10 having through-holes 12 whose size is selected depending on the size of the nuclei of the nucleated cells is provided. Specifically, in the filtration method using the filter 10, a filter 10 having through-holes 12 smaller than the size of the nuclei of the nucleated cells to be filtered is selected and provided for filtration. Thus, the filtration method using the filter 10 allows the nucleated cells to be reliably captured on the filter 10, thus improving the recovery thereof.

Although an example in which the dimensions of the through-holes 12 are substantially identical has been described in the first embodiment, this should not be construed as limiting. For example, the through-holes 12 may have different dimensions, provided that the maximum dimension of the through-holes 12 is set to be smaller than the size of the nuclei of the nucleated cells.

Although an example in which the method for manufacturing the filter 10 includes the step of forming a backing layer body has been described in the first embodiment, this should not be construed as limiting. For example, the method for manufacturing the filter 10 need not include the step of forming a backing layer body.

Although an example in which a liquid containing nucleated cells is passed through the filter 10 to filter the nucleated cells has been described in the first embodiment, this should not be construed as limiting. For example, the filter 10 may be used to separate living cells and dead cells from a liquid containing living cells and dead cells.

In an example method for separating living cells and dead cells, the filter 10 may capture living cells on the first main surface PS1 of the filter section 11 while allowing dead cells to pass therethrough. Alternatively, the filter 10 may capture dead cells on the first main surface PS1 of the filter section 11 while allowing living cells to pass therethrough.

Although the filter 10 and the filtration method have been described in the first embodiment, this should not be construed as limiting. For example, a kit for performing the filtration method that includes the filter 10 for filtration of nucleated cells may be used.

EXAMPLES

The filter 10 according to the first embodiment was evaluated for performance using Examples 1 to 8 and Comparative Example 1.

(1) Filters of Examples 1 to 8 and Comparative Example 1

The filter 10 according to the first embodiment was fabricated according to the specifications shown in Table 1.

TABLE 1

|  | Example 1 | Example 2 | Example 3 | Example 4 | Example 5 | Example 6 | Example 7 | Example 8 | Comparative Example 1 |
| --- | --- | --- | --- | --- | --- | --- | --- | --- | --- |
| Hole size (length d on one side of each through-hole) (μm) | 0.4 | 0.5 | 1.2 | 1.9 | 2.5 | 3.6 | 4.5 | 1.9 | 7.2 |
| Standard deviation of hole size | 0.1 | 0.2 | 0.2 | 0.2 | 0.3 | 0.4 | 0.5 | 0.2 | 0.7 |
| Coefficient of variation of hole size | 0.25 | 0.40 | 0.17 | 0.11 | 0.12 | 0.11 | 0.11 | 0.11 | 0.09 |
| Grid pitch b (μm) | 0.8 | 1.0 | 1.7 | 2.6 | 3.6 | 5.2 | 6.5 | 2.6 | 10.4 |
| Standard deviation of grid pitch | 0.2 | 0.2 | 0.2 | 0.3 | 0.4 | 0.5 | 0.7 | 0.3 | 1.0 |
| Diameter of inscribed circle of each through-hole (μm) | 0.4 | 0.5 | 1.2 | 1.9 | 2.5 | 3.6 | 4.5 | 1.9 | 7.2 |
| Number of through-holes (holes) | $44.2 \times 10^6$ | $28.3 \times 10^6$ | $9.1 \times 10^6$ | $4.2 \times 10^6$ | $2.2 \times 10^6$ | $1.0 \times 10^6$ | $6.7 \times 10^5$ | $4.2 \times 10^6$ | $2.6 \times 10^5$ |
| Open area percentage (%) | 23.3 | 23.3 | 46.0 | 53.4 | 48.2 | 47.9 | 47.9 | 53.4 | 47.9 |
| Thickness (μm) | 0.6 | 0.6 | 0.8 | 0.8 | 0.8 | 0.8 | 1.7 | 0.8 | 1.8 |

In Examples 1 to 8 and Comparative Example 1, the diameter of the outer shape was 7.8 mm, and the diameter of the filter section 11 was 6 mm. In Examples 1 to 7, the filter body 14 was formed of nickel (Ni). In Example 8, the filter body 14 was formed of gold (Au). The filter section 11 had square through-holes 12 arranged in a square grid array as viewed from the first main surface PS1 side. Since the through-holes 12 had a square shape, as shown in Table 1, the length d on one side of each through-hole 12 was equal to the diameter of the inscribed circle of each through-hole 12.

Figure 4:
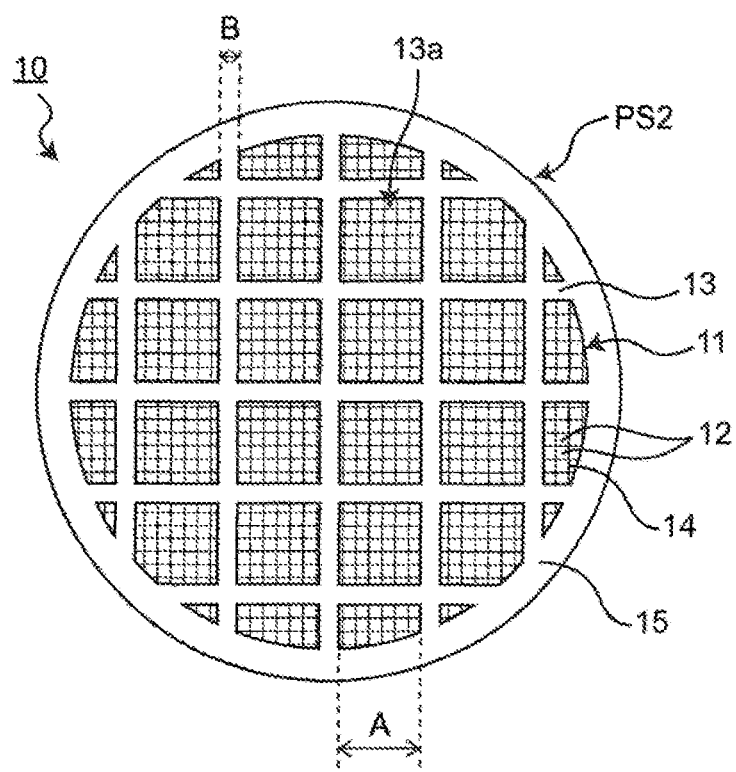
FIG. 4 is a schematic view of the filter according to the first embodiment of the present invention, with a support substrate provided thereon.

FIG. 4 schematically illustrates the configuration of the filter 10, with a support substrate 13 attached thereto. As shown in FIG. 4, in Examples 1 to 6, the support substrate 13 was disposed on the second main surface PS2 side of the filter 10. The support substrate 13 had a plurality of square openings 12a. The thickness of the support substrate 13 was 14 µm. The length on one side of each opening 13a, i.e., the strip spacing A, was 260 µm. The strip width B was 14 µm.

These filters of Examples 1 to 8 and Comparative Example 1 were evaluated for performance by installing each of the filters of Examples 1 to 8 and Comparative Example 1 in a filtration apparatus and filtering a cell suspension.

(2) Cell Suspension

Suspended cells, namely, HL-60, which is a leukemia cell line, were cultured in RPMI 1620 medium (with L-glutamine) containing 10% by volume fetal bovine serum and 1% by volume penicillin-streptomycin in a 100 mm dish for 5 days.

A portion of the culture solution was transferred from the 100 mm dish to a 15 mL centrifuge tube by pipetting. The centrifuge tube containing the culture solution was then centrifuged at a rotational speed of 1,000 rpm for 3 minutes, followed by removing the supernatant. Phosphate-buffered saline was then added to prepare a cell suspension. The amount of phosphate-buffered saline added was adjusted so that the cell suspension had a cell concentration of $10^5$ cells/mL.

In a microtube, 30 µL of the cell suspension and 15 µL of a fluorescent reagent, namely, DAPI, were mixed to stain the cells. The suspension containing the stained cells (stained cell suspension) was incubated in dark at 37° C. for 20 minutes. A 10 µL drop of the stained cell suspension was then deposited on a slide glass, and a cover glass was placed thereon. Fluorescence was observed under a fluorescence microscope using an excitation light source with a wavelength of 345 nm through a bandpass filter centered at 455 nm. The size of the nuclei of the HL-60 cells that appeared blue-violet was measured to be 7.0 µm in diameter. In the examples, the size of the nuclei of the HL-60 cells is the average size calculated from the measured sizes of the nuclei of 100 HL-60 cells.

After the cells in a portion of the culture solution in the 100 mm dish were dispersed by pipetting, 10 µL of the culture solution was taken using a micropipette, and the cell concentration, the survival rate, and the average cell size were measured using a cell counter (Countess (registered trademark) II FL automated cell counter available from Thermo Fisher Scientific Inc.). As a result, the cell concentration was $5 \times 10^5$ cells/mL, the average size of active cells (HL-60) was 13.4 µm, and the survival rate was 90%. Specifically, the cell suspension and a 0.4% trypan blue solution were mixed in a volume ratio of 1:1 to strain the cell membrane in blue. A 10 µL drop of the mixture of the cell suspension and the trypan blue solution was deposited on a cell counting side (Countess (registered trademark) cell counting chamber slide available from Thermo Fisher Scientific Inc.), and the cell morphology was observed. In the cell counting, the cell count (concentration), the average cell size, and the survival rate were determined by image analysis using the stained cell membrane as a marker.

The culture solution in the 100 mm dish was further mixed with the RPMI 1620 medium in a certain ratio to prepare the following HL-60 cell suspension:

Active cell (HL-60) concentration . . . $3.06 \times 10^5$ cells/mL

Liquid volume . . . 1 mL

The cell survival rate was measured by the method described above after the culture solution in the 100 mm dish was allowed to stand in a clean bench at room temperature for 4 hours. As a result, the survival rate decreased to 81%. This means that the activity of cells decreases after the cells are allowed to stand at room temperature for an extended period of time.

(3) Filtration Method

The cell suspension was filtered through each of the filters of Examples 1 to 8 and Comparative Example 1 attached to the filtration apparatus by bringing the cell suspension into contact with the first main surface PS1 of the filter section 11 and applying suction from the second main surface PS2 side. The operating conditions included applying suction at a pressure of 2 kPa.

(4) Evaluation Results

Table 2 shows the evaluation results.

TABLE 2

|  | Example 1 | Example 2 | Example 3 | Example 4 | Example 5 | Example 6 | Example 7 | Example 8 | Comparative Example 1 |
|---|---|---|---|---|---|---|---|---|---|
| X: diameter of inscribed circle of each through-hole (µm) | 0.4 | 0.5 | 1.2 | 1.9 | 2.5 | 3.6 | 4.5 | 1.9 | 7.2 |
| Cell |  |  |  |  | HL-60 |  |  |  |  |
| Number of supplied active cells ($\times 10^5$ cells) |  |  |  | 3.06 |  |  |  | 3.21 | 3.06 |
| Y: size of cell nuclei (µm) |  |  |  |  | 7.0 |  |  |  |  |
| X/Y | 0.06 | 0.07 | 0.17 | 0.27 | 0.35 | 0.51 | 0.64 | 0.27 | 1.03 |
| Time required for filtration (seconds) | 468 | 168 | 71 | 53 | 16 | 12 | 3 | 69 | 2 |
| Filtrate volume (mL) | 0.84 | 0.78 | 0.81 | 0.91 | 0.82 | 0.91 | 0.93 | 0.85 | 0.88 |
| Total number of cells in filtrate ($\times 10^5$ cells) | 0 | 0 | 0 | 0 | 0 | 0 | 0 | 0 | 1.45 |
| Percentage of active cells among all cells in filtrate (%) | 0 | 0 | 0 | 0 | 0 | 0 | 0 | 0 | 68 |
| Number of active cells present in filtrate ($\times 10^5$ cells) | 0 | 0 | 0 | 0 | 0 | 0 | 0 | 0 | 0.99 |
| Recovery (%) | 100 | 100 | 100 | 100 | 100 | 100 | 100 | 100 | 67.6 |

In Examples 1 to 8, the recovery of the cells (HL-60) was 100%. In contrast, in Comparative Example 1, the recovery of the cells was 67.6%. In Comparative Example 1, the cells passed through the through-hole 12 probably because the diameter of the inscribed circle of each through-hole 12 was 7.2 μm, which is larger than the size of the nuclei of the cells (HL-60), i.e., 7.0 μm. In contrast, in Examples 1 to 8, more cells were captured on the first main surface PS1 of the filter section 11 than in Comparative Example 1 probably because the diameter of the inscribed circle of each through-hole 12 ranged from 0.4 μm to 4.5 μm, which is smaller than the size of the nuclei of the cells. As used herein, the term "recovery" refers to the proportion of the number of supplied active cells to the number of cells captured on the first main surface PS1 of the filter, which was calculated as (number of supplied active cells−number of active cells present in filtrate)/(number of supplied active cells). In Table 2, the concentration of active cells (HL-60) differs between Examples 1 to 7 and Comparative Example 1 and Example 8 since they were evaluated on different dates, which does not affect the evaluation results.

The number of active cells present in the filtrate was determined as follows. After the cells in the filtrate were dispersed by pipetting, ten 10 μL samples of the filtrate were taken using a micropipette, and the number of cells in each sample was counted using a cell counter (Countess (registered trademark) II FL automated cell counter available from Thermo Fisher Scientific Inc.).

Thus, if the diameter of the inscribed circle of each through-hole 12 is set to be smaller than the size of the cell nuclei, more cells can be captured, thus improving the recovery thereof. This is because, whereas the cytoplasm surrounding the cell nuclei is easily deformed, the cell nuclei are resistant to deformation.

If the diameter of the inscribed circle of each through-hole 12 is larger than the size of the cell nuclei, as in Comparative Example 1, the cells may pass through the filter 10 as a result of deformation of the cytoplasm, even if the diameter of the inscribed circle of each through-hole 12 is smaller than the size of the cells.

In contrast, if the diameter of the inscribed circle of each through-hole 12 is set to be smaller than the size of the cell nuclei, as in Examples 1 to 8, the cells can be more easily captured on the filter 10 than in Comparative Example 1 since the cell nuclei are resistant to deformation.

The fact that the filter 10 was formed of a metal also contributed to improved cell recovery. The use of a metal filter 10 results in less deformation of the through-holes 12 in the filter 10 than the use of a resin filter such as a membrane filter. The filter 10 can therefore more easily capture the cells.

As shown in Table 2, to improve the cell recovery, it is preferred that the ratio of the diameter of the inscribed circle of each through-hole 12 (X) to the size of the nuclei of the cells (Y) be 0.64 or less. It is also preferred that the ratio of the diameter of the inscribed circle of each through-hole 12 (X) to the size of the nuclei of the cells (Y) be 0.06 or more.

As shown in Table 2, the filtration time of Example 1 was longer than those of Examples 2 to 7. This indicates that the filtration time can be shortened if the ratio of the diameter of the inscribed circle of each through-hole 12 (X) to the size of the nuclei of the cells (Y) is 0.07 or more.

The area of the portions of the filter section 11 where the through-holes 12 were provided in Examples 1 to 8 was 0.28 cm$^2$. The treatment capacity (number of supplied cells/area of portions where through-holes are provided) was $1.1 \times 10^6$ cells/cm$^2$. In contrast, the treatment capacity of the filter in Patent Document 1 is $0.37 \times 10^6$ cells/cm$^2$. Thus, the filters of Examples 1 to 8 had higher treatment capacity than the filter in Patent Document 1.

It should also be understood that it is preferred to reduce contamination of the cell suspension with impurities, specifically, dissolution of the metal forming the filter 10 in the cell suspension, during the filtration of the nucleated cells.

In Examples 1 to 7, a metal filter formed of nickel was used to filter the cells (HL-60). In Examples 1 to 7, filtration was completed without impairing the activity of the cells. In Example 8, a metal filter formed of Au was used to filter the cells (HL-60). In Example 8, as in Examples 1 to 7, filtration was completed without impairing the activity of the cells.

The immersion potential of nickel and Au, which is a measure of the ionization tendency of metals, was measured. The immersion potential of nickel and Au in phosphate-buffered saline was measured with respect to a silver chloride reference electrode immersed in a saturated potassium chloride solution for 3 minutes. As a result, the immersion potential of nickel remained within a range higher than 0.03 V, and the immersion potential of Au remained within a range higher than 0.3 V. Thus, it can be concluded that the use of a metal and/or metal oxide that exhibits an immersion potential of at least higher than 0.03 V as measured under the same conditions allows filtration without impairing the activity of the cells.

In Examples 1 to 8, HL-60 was captured on the first main surface PS1 of the filter section 11 while phosphate-buffered saline passed therethrough. The ease with which liquid passes through a filter depends on the open area percentage of the filter. Of the examples. Examples 1 and 2 had the lowest open area percentage, i.e., 23.3% (see Table 1). Thus, it can be concluded that a metal filter according to the present invention that has an open area percentage of at least 23.3% allows liquid to pass therethrough. From the viewpoint of ease of passage of liquid, it is also preferred that the through-holes 12 formed in the metal filter have less variation. Of the examples with short filtration times (e.g., less than 100 seconds), Example 3 had the highest coefficient of variation, i.e., 0.17. Thus, it can be concluded that a coefficient of variation of 0.17 or less is preferred.

(5) Filters of Examples 9 to 16

The filer 10 according to the first embodiment was fabricated according to the specifications shown in Table 3.

TABLE 3

|  | Example 9 | Example 10 | Example 11 | Example 12 | Example 13 | Example 14 | Example 15 | Example 16 |
|---|---|---|---|---|---|---|---|---|
| Hole size (length d on one side of each through-hole) (μm) | 0.4 | 1.2 | 1.9 | 2.5 | 3.6 | 4.5 | 7.2 | 1.9 |
| Standard deviation of hole size | 0.1 | 0.2 | 0.2 | 0.3 | 0.4 | 0.5 | 0.7 | 0.2 |
| Coefficient of variation of hole size | 0.25 | 0.17 | 0.11 | 0.12 | 0.11 | 0.11 | 0.09 | 0.11 |
| Grid pitch b (μm) | 0.9 | 1.7 | 2.6 | 3.6 | 5.2 | 6.5 | 10.4 | 2.6 |

TABLE 3-continued

|  | Example 9 | Example 10 | Example 11 | Example 12 | Example 13 | Example 14 | Example 15 | Example 16 |
|---|---|---|---|---|---|---|---|---|
| Standard deviation of grid pitch | 0.2 | 0.2 | 0.3 | 0.4 | 0.5 | 0.7 | 1 | 0.3 |
| Diameter of inscribed circle of each through-hole (μm) | 0.4 | 1.2 | 1.9 | 2.5 | 3.6 | 4.5 | 7.2 | 1.9 |
| Number of through-holes (holes) | $44.2 \times 10^6$ | $9.1 \times 10^6$ | $4.2 \times 10^6$ | $2.2 \times 10^6$ | $1.0 \times 10^6$ | $6.7 \times 10^5$ | $9.1 \times 10^5$ | $4.2 \times 10^6$ |
| Open area percentage (%) | 18.4 | 46 | 53.4 | 48.2 | 47.9 | 47.9 | 47.9 | 53.4 |
| Thickness (μm) | 0.6 | 0.8 | 0.8 | 0.8 | 0.8 | 1.7 | 1.8 | 0.8 |

In Examples 9 to 16, the diameter of the outer shape was 7.8 mm, and the diameter of the filter section 11 was 6 mm. In Examples 9 to 15, the filter body 14 was formed of nickel. In Example 16, the filter body 14 was formed of Au. The filter section 11 had square through-holes 12 arranged in a square grid array as viewed from the first main surface PS1 side. Since the through-holes 12 had a square shape, as shown in Table 3, the length d on one side of each through-hole 12 was equal to the diameter of the inscribed circle of each through-hole 12.

(6) Cell Suspension

The following two cell suspensions were prepared.

(i) Hela Suspension

Adherent cells, namely, Hela, which is a human cell line derived from human cervical cancer, were cultured in RPMI 1620 medium (with L-glutamine) containing 10% by volume fetal bovine serum and 1% by volume penicillin-streptomycin in a 100 mm dish for 5 days.

After the culture, the medium was removed from the 100 mm dish by suction. To the Hela cells in the 100 mm dish was then added 2 mL of phosphate-buffered saline, and the cell culture surface (cell surface) of the Hela cells was washed by pipetting. To the Hela cells was further added 1 mL of phosphate-buffered saline, and the cell culture surface of the Hela cells was washed again by pipetting, followed by removing the PBS by suction. To the washed Hela cells was then added 0.8 mL of a 0.25% trypsin/0.02% EDTA solution, and the Hela cells were allowed to stand in a $CO_2$ incubator for 5 minutes. After it was confirmed under a microscope that the Hela cells were separated from the 100 mm dish, a portion of the cell suspension was transferred from the 100 mm dish to a 15 mL centrifuge tube by pipetting. The 100 mm dish was then washed with 1 mL of the medium, and a portion of the cell suspension was transferred to the centrifuge tube. The centrifuge tube was centrifuged using a centrifuge at 1,000 rpm for 5 minutes, followed by removing the supernatant. The cells were then dispersed by pipetting with 1 mL of the medium.

The size of the nuclei of the Hela cells was measured by magnification observation of a portion of the cell suspension under a microscope equipped with an objective micrometer at 40× magnification. The size of the nuclei of the Hela cells was 10.0 μm in diameter. In the examples, the size of the nuclei of the Hela cells is the average size calculated from the measured sizes of the nuclei of 100 Hela cells.

Using a micropipette, 10 μL of the cell suspension was taken, and the cell concentration, the survival rate, and the average cell size were measured using a cell counter (Countess (registered trademark) II FL automated cell counter available from Thermo Fisher Scientific Inc.). As a result, the cell concentration was $7 \times 10^6$ cells/mL, the average size of active cells (Hela) was 17.1 μm, and the survival rate was 95%. Specifically, the cell suspension and a 0.4% trypan blue solution were mixed in a volume ratio of 1:1 to strain the cell membrane in blue. A 10 μL drop of the mixture of the cell suspension and the trypan blue solution was deposited on a cell counting slide (Countess (registered trademark) cell counting chamber slide available from Thermo Fisher Scientific Inc.), and the cell morphology was observed. In the cell counting, the cell count (concentration), the average cell size, and the survival rate were determined by image analysis using the stained cell membrane as a marker.

The cell suspension containing the cultured Hela cells was diluted with the RPMI 1620 medium to prepare a Hela cell suspension.

(ii) Ras-Gene-Transfected NIH3T3 (Hereinafter also Referred to as NIH3T3(ras)) Suspension Adherent cells, namely, NIH3T3(ras), which is a ras-gene-transfected mouse embryonic fibroblast line, were cultured in DMEK medium (with 4.5 g/L glucose L-glutamate) containing 5% by volume fetal bovine serum and 1% by volume penicillin-streptomycin in a 100 mm dish for 3 days.

After the culture, the medium was removed from the 100 mm dish by suction. To the NIH3T3(ras) cells remaining in the 100 mm dish was then added 2 mL of phosphate-buffered saline, and the cell culture surface (cell surface) was washed by pipetting. To the NIH3T3(ras) cells was further added 1 mL of phosphate-buffered saline, and the cell culture surface was washed again by pipetting, followed by removing the PBS by suction. To the NIH3T3(ras) cells was then added 0.8 mL of a 0.25% trypsin/0.02% EDTA solution, and the NIH3T3(ras) cells were allowed to stand in a $CO_2$ incubator for 3 minutes. After it was confirmed under a microscope that the cells were separated from the 100 mm dish, a portion of the cell suspension was transferred from the 100 mm dish to a 15 mL centrifuge tube by pipetting. The 100 mm dish was then washed with 1 mL of the medium, and a portion of the cell suspension was transferred to the centrifuge tube. The centrifuge tube was centrifuged using a centrifuge at 1,000 rpm for 5 minutes, followed by removing the supernatant. The cells were then dispersed by pipetting with 1 mL of the medium.

The size of the nuclei of the NIH3T3(ras) cells was measured by magnification observation of a portion of the cell suspension under a microscope equipped with an objective micrometer at 40× magnification. The size of the nuclei of the NIH3T3(ras) cells was 11.5 μm in diameter. In the examples, the size of the nuclei of the NIH3T3(ras) cells is the average size calculated from the measured sizes of the nuclei of 100 NIH3T3(ras) cells.

Using a micropipette, 10 μL of the cell suspension was taken, and the cell concentration, the survival rate, and the average cell size were measured using a cell counter (Countess (registered trademark) II FL automated cell counter available from Thermo Fisher Scientific Inc.). As a result, the cell concentration was $4\times10^6$ cells/mL, the average size of active cells (NIH3T3(ras)) was 15.4 μm, and the survival rate was 89%. Specifically, the cell suspension and a 0.4% trypan blue solution were mixed in a volume ratio of 1:1 to strain the cell membrane in blue. A 10 μL drop of the mixture of the cell suspension and the trypan blue solution was deposited on a cell counting slide (Countess (registered trademark) cell counting chamber slide available from Thermo Fisher Scientific Inc.), and the cell morphology was observed. In the cell counting, the cell count (concentration), the average cell size, and the survival rate were determined by image analysis using the stained cell membrane as a marker.

The cell suspension containing the cultured NIH3T3(ras) cells was diluted with the DMEM medium (with 4.5 g/L glucose L-glutamate) to prepare a NIH3T3(ras) cell suspension.

The sizes of the nuclei of the Hela cells and the NIH3T3 (ras) cells were also measured under a fluorescence microscope. Specifically, the sizes of the nuclei of the Hela cells and the NIH3T3(ras) cells were measured by magnification observation of a portion of each cell suspension under a fluorescence microscope at 40× magnification. The size of the nuclei of the Hela cells was measured to be 10.0 μm in diameter under a fluorescence microscope, and the size of the nuclei of the NIH3T3(ras) cells was measured to be 11.5 μm.

Using a micropipette, 10 μL of each cell suspension was taken, and the cell concentration, the survival rate, and the average cell size were measured using a cell counter (Countess (registered trademark) II FL automated cell counter available from Thermo Fisher Scientific Inc.). As a result, the cell concentration was $3.17\times10^5$ cells/mL for Hela and was $2.97\times10^5$ cells/mL for NIH3T3(ras), the average size of active cells was 17.1 μm for Hela and was 15.4 μm for NIH3T3(ras), and the survival rate was 98% for Hela and was 89% for NIH3T3(ras). Specifically, each cell suspension and a 0.4% trypan blue solution were mixed in a volume ratio of 1:1 to strain the cell membrane in blue. A 10 μL drop of the mixture of the cell suspension and the trypan blue solution was deposited on a cell counting slide (Countess (registered trademark) cell counting chamber slide available from Thermo Fisher Scientific Inc.), and the cell morphology was observed. In the cell counting, the cell count (concentration), the average cell size, and the survival rate were determined by image analysis using the stained cell membrane as a marker.

The cell suspension containing the Hela cells was further mixed with phosphate-buffered saline in a certain ratio to prepare the following Hela cell suspension:
Active cell (Hela) concentration . . . $3.17\times10^5$ cells/mL
Liquid volume . . . 1 mL The cell suspension containing NIH3T3(ras) was further mixed with phosphate-buffered saline in a certain ratio to prepare the following NIH3T3(ras) cell suspension:
Active cell (NIH3T3(ras)) concentration . . . $2.98\times10^5$ cells/mL
Liquid volume . . . 1 mL (7) Filtration Method Each cell suspension was filtered through each of the filters of Examples 9 to 16 attached to the filtration apparatus by bringing the cell suspension into contact with the first main surface PS1 of the filter section 11 and applying suction from the second main surface PS2 side. The operating conditions included applying suction at a pressure of 2 kPa.

(8) Evaluation Results

Tables 4 and 5 show the evaluation results.

TABLE 4

| | Example 9 | Example 10 | Example 11 | Example 12 | Example 13 | Example 14 | Example 15 | Example 16 |
|---|---|---|---|---|---|---|---|---|
| X: diameter of inscribed circle of each through-hole (μm) | 0.4 | 1.2 | 1.9 | 2.5 | 3.6 | 4.5 | 7.2 | 1.9 |
| Cell | | | | Hela | | | | |
| Number of supplied active cells ($\times10^5$ cells) | | | | 3.17 | | | | 2.99 |
| Y: size of cell nuclei (μm) | | | | 10 | | | | |
| X/Y | 0.04 | 0.12 | 0.19 | 0.25 | 0.36 | 0.45 | 0.72 | 0.19 |
| Time required for filtration (seconds) | 1,320 | 699 | 489 | 470 | 369 | 233 | 169 | 483 |
| Filtrate volume (mL) | 0.79 | 0.87 | 0.90 | 0.87 | 0.85 | 0.93 | 0.79 | 0.85 |
| Total number of cells in filtrate ($\times10^5$ cells) | 0 | 0 | 0 | 0 | 0 | 0 | 0 | 0 |
| Percentage of active cells among all cells in filtrate (%) | 0 | 0 | 0 | 0 | 0 | 0 | 0 | 0 |
| Number of active cells present in filtrate ($\times10^5$ cells) | 0 | 0 | 0 | 0 | 0 | 0 | 0 | 0 |
| Recovery (%) | 100 | 100 | 100 | 100 | 100 | 100 | 100 | 100 |

TABLE 5

|  | Example 9 | Example 10 | Example 11 | Example 12 | Example 13 | Example 14 | Example 15 | Example 16 |
|---|---|---|---|---|---|---|---|---|
| X: diameter of inscribed circle of each through-hole (μm) | 0.4 | 1.2 | 1.9 | 2.5 | 3.6 | 4.5 | 7.2 | 1.9 |
| Cell | | | | NIH3T3(ras) | | | | |
| Number of supplied active cells ($\times 10^5$ cells) | | | | 2.97 | | | | |
| Y: size of cell nuclei (μm) | | | | 11.5 | | | | |
| X/Y | 0.03 | 0.10 | 0.17 | 0.22 | 0.31 | 0.39 | 0.63 | 0.17 |
| Time required for filtration (seconds) | 1,800 | 986 | 600 | 374 | 360 | 115 | 15 | 540 |
| Filtrate volume (mL) | 0.48 | 0.85 | 0.92 | 0.95 | 0.86 | 0.92 | 0.94 | 0.87 |
| Total number of cells in filtrate ($\times 10^5$ cells) | 0 | 0 | 0 | 0 | 0 | 0 | 0 | 0 |
| Percentage of active cells among all cells in filtrate (%) | 0 | 0 | 0 | 0 | 0 | 0 | 0 | 0 |
| Number of active cells present in filtrate ($\times 10^5$ cells) | 0 | 0 | 0 | 0 | 0 | 0 | 0 | 0 |
| Recovery (%) | 100 | 100 | 100 | 100 | 100 | 100 | 100 | 100 |

As shown in Tables 4 and 5, in Examples 9 to 16, the recovery was 100% for both Hela and NIH3T3(ras). In Examples 9 to 16, as in Examples 1 to 8, more cells were captured on the first main surface PS1 of the filter section 11 probably because the diameter of the inscribed circle of each through-hole 12 ranged from 0.4 μm to 7.2 μm, which is smaller than the sizes of the nuclei of the Hela cells and the NIH3T3(ras) cells.

As shown in Tables 4 and 5, the filtration time of Example 9 was longer than those of Examples 10 to 16. As in Examples 1 to 8, this indicates that the filtration time can be shortened if the ratio of the diameter of the inscribed circle of each through-hole 12 (X) to the size of the nuclei of the cells (Y) is 0.07 or more.

The area of the portions of the filter section 11 where the through-holes 12 were provided in Examples 9 to 16 was 0.28 cm². The treatment capacity (number of supplied cells/area of portions where through-holes are provided) was $1.1 \times 10^6$ cells/cm². In contrast, the treatment capacity of the filter in Patent Document 1 is $0.37 \times 10^6$ cells/cm². Thus, the filters of Examples 1 to 8 had higher treatment capacity than the filter in Patent Document 1.

In Examples 9 to 15, a metal filter formed of nickel was used. In Example 16, a metal filter formed of Au was used. As in Examples 1 to 8, filtration was completed without impairing the activity of the cells.

Although examples in which cell suspensions containing relatively high concentrations of nucleated cells, i.e., $10^5$ cells/mL or more, were filtered to capture the nucleated cells have been described in the examples, cell suspensions containing extremely low concentrations of nucleated cells, i.e., on one order of several cells/mL, can also be filtered through the filter 10 to capture the nucleated cells to be recovered.

Although preferred embodiments of the present invention have been sufficiently described with reference to the accompanying drawings, various changes and modifications will be apparent to those skilled in the art. Such changes and modifications are to be understood as being included within the scope of the invention as defined by the appended claims without departing therefrom.

A filter according to the present invention allows for improved recovery of nucleated cells and is therefore useful for applications in which nucleated cells are separated from cell suspensions.

REFERENCE SIGNS LIST 10 filter
11 filter section
12 through-hole
13 support substrate
13a opening
14 filter body
15 frame section
PS1 first main surface
PS2 second main surface

The invention claimed is:

1. A method for filtration of nucleated cells, the method comprising:
obtaining a size of nuclei of the nucleated cells to be filtered;
selecting a filter based on the obtained size of the nuclei of the nucleated cells to be filtered, the filter comprising at least one of a metal and a metal oxide as a major component thereof and having a plurality of through-holes therein, each of the plurality of through-holes having a square shape, wherein the selected filter has a diameter of an inscribed circle of each of the plurality of through-holes that is smaller than the size of nuclei of the nucleated cells to be filtered, the inscribed circle of each of the plurality of through-holes touching all sides defining an opening of the through-hole; and
passing a liquid containing the nucleated cells through the filter.

2. The filtration method according to claim 1, wherein a ratio of the diameter of the inscribed circle of each of the plurality of through-holes to the size of the nuclei of the nucleated cells is 0.06 to 0.64.

3. The filtration method according to claim 1, wherein a ratio of the diameter of the inscribed circle of each through-hole to the size of the nuclei of the nucleated cells is 0.06 or more.

4. The filtration method according to claim 1, wherein a ratio of the diameter of the inscribed circle of each through-hole to the size of the nuclei of the nucleated cells is 0.07 or more.

5. The filtration method according to claim 1, wherein an immersion potential of the at least one of the metal and the metal oxide in phosphate-buffered saline is higher than 0.03 V with respect to a silver chloride reference electrode immersed in a saturated potassium chloride solution.

6. The filtration method according to claim 1, wherein the at least one of the metal and the metal oxide comprises at least one selected from the group of gold, silver, copper, platinum, nickel, palladium, and alloys and oxides thereof.

7. The filtration method according to claim 1, wherein the step of passing the liquid containing the nucleated cells through the filter comprises separating living cells and dead cells.

8. The filtration method according to claim 1, wherein a coefficient of variation of a size of the plurality of through-holes in the filter is 0.17 or less.

\* \* \* \* \*